(12) United States Patent
Machida et al.

(10) Patent No.: US 11,642,695 B2
(45) Date of Patent: May 9, 2023

(54) ULTRASONIC PROBE AND ULTRASONIC MEASUREMENT APPARATUS USING THE SAME

(71) Applicant: Hitachi, Ltd., Tokyo (JP)

(72) Inventors: Shuntaro Machida, Tokyo (JP); Akifumi Sako, Tokyo (JP); Yasuhiro Yoshimura, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 284 days.

(21) Appl. No.: 16/768,863

(22) PCT Filed: Aug. 23, 2018

(86) PCT No.: PCT/JP2018/031066
§ 371 (c)(1),
(2) Date: Jun. 1, 2020

(87) PCT Pub. No.: WO2019/187197
PCT Pub. Date: Oct. 3, 2019

(65) Prior Publication Data
US 2021/0162462 A1    Jun. 3, 2021

(30) Foreign Application Priority Data
Mar. 28, 2018    (JP) .............................. JP2018-061219

(51) Int. Cl.
*B06B 1/02* (2006.01)
*A61B 8/00* (2006.01)
(Continued)

(52) U.S. Cl.
CPC .......... *B06B 1/0292* (2013.01); *A61B 8/4444* (2013.01); *A61B 8/54* (2013.01);
(Continued)

(58) Field of Classification Search
None
See application file for complete search history.

(56) References Cited

U.S. PATENT DOCUMENTS

2005/0199995 A1* 9/2005 Nomoto ................... H01L 23/34
257/692
2015/0365017 A1   12/2015 Kandori
(Continued)

FOREIGN PATENT DOCUMENTS

JP    201615723 A    1/2016
JP    201747109 A    3/2017

OTHER PUBLICATIONS

Search Report dated Oct. 16, 2019 in correspondnig International Application PCT/JP2018/031066.

*Primary Examiner* — Yi-Shan Yang
(74) *Attorney, Agent, or Firm* — Miles & Stockbridge, P.C.

(57) ABSTRACT

An ultrasonic probe includes a semiconductor chip in which an ultrasonic transducer is formed and an electrode pad electrically connected to an upper electrode or a lower electrode of the ultrasonic transducer is provided and a flexible substrate in which a bump electrically connected to the electrode pad is provided and the bump is disposed in a portion overlapping with a stepped portion of the semiconductor chip. Further, a height of a connection surface of the electrode pad of the semiconductor chip connected to the bump is lower than a height of a lower surface of the lower electrode.

12 Claims, 9 Drawing Sheets

(51) Int. Cl.
*H01L 23/498* (2006.01)
*H01L 23/00* (2006.01)

(52) U.S. Cl.
CPC .......... *H01L 23/4985* (2013.01); *H01L 24/08* (2013.01); *B06B 2201/76* (2013.01); *H01L 2224/16227* (2013.01)

(56) References Cited

U.S. PATENT DOCUMENTS

2016/0058417 A1* 3/2016 Kiyose .................... B06B 1/067 600/459
2017/0067856 A1* 3/2017 Kandori ............. G01N 29/2406

* cited by examiner

ULTRASONIC PROBE AND ULTRASONIC MEASUREMENT APPARATUS USING THE SAME

TECHNICAL FIELD

The present invention relates to an ultrasonic probe and an ultrasonic measurement apparatus using the same.

BACKGROUND ART

As a structure in which a semiconductor chip (CMUT chip) having capacitive micro-machined ultrasonic transducers (CMUT) formed therein is mounted in a probe (ultrasonic probe), a structure in which the CMUT chip and a flexible substrate are electrically connected by wire bonding has been known. In this structure, a height difference occurs between a front surface of the semiconductor chip and an apex of the wire loop. Therefore, in an acoustic lens disposed on the CMUT chip, the lens thickness of a portion corresponding to a cell region of the CMUT is larger than that of a portion other than the cell region. In the acoustic lens mentioned above, if the lens thickness of the portion corresponding to the cell region of the CMUT is large, the attenuation of the ultrasonic waves becomes large (particularly, high frequency components), which hinders the improvement in acoustic pressure and the increase in frequency.

Therefore, in the connection between the CMUT chip and the flexible substrate, the electrical connection by the flip-chip bonding method instead of the wire bonding method has been studied.

Note that Japanese Patent Application Laid-Open Publication No. 2016-15723 (Patent Document 1) discloses a structure in which a CMUT chip and a flexible substrate are electrically connected to each other by projecting connection electrodes.

RELATED ART DOCUMENTS

Patent Documents

Patent Document 1: Japanese Patent Application Laid-Open Publication No. 2016-15723

SUMMARY OF THE INVENTION

Problems to be Solved by the Invention

When the electrical connection between the CMUT chip and the flexible substrate is made by the flip-chip bonding, the number of electrode pads provided on the main surface of the CMUT chip may be as large as several hundreds, and it is thus difficult to align the electrode pads with connection conductor portions of the flexible substrate. In this case, it is possible to reduce the difficulty of the alignment by increasing the pad diameter of the electrode pads of the CMUT chip. However, if the pad diameter of the electrode pads is increased, the chip size increases and the probe becomes larger. Namely, it is not possible to reduce the size of the probe.

Further, in the structure of the probe, the lens disposed on the cell region of the CMUT preferably has a small thickness as described above.

Note that Patent Document 1 above does not particularly mention the method of aligning the electrode pads of the CMUT chip with the electrodes of the flexible substrate. In addition, with respect to the chip thickness of the CMUT chip, there is no particular mention about the chip thickness of the cell region of the CMUT and the chip thickness of the connection portion with the flexible substrate.

An object of the present invention is to provide a technology capable of facilitating the alignment at the time of flip-chip bonding between a semiconductor chip and a flexible substrate, and further improving measurement accuracy by an ultrasonic probe and an ultrasonic measurement apparatus.

The above object and novel feature of the present invention will be apparent from the description of this specification and the accompanying drawings.

Means for Solving the Problems

The following is a brief description of an outline of a typical embodiment disclosed in this application.

An ultrasonic probe according to an embodiment includes: a semiconductor chip in which an ultrasonic transducer is formed and an electrode pad electrically connected to an upper electrode or a lower electrode of the ultrasonic transducer is provided; and a flexible substrate in which a connection conductor portion electrically connected to the electrode pad is provided and the connection conductor portion is disposed in a portion overlapping with a part of the semiconductor chip in a plan view. Further, in the ultrasonic probe, a height of a connection surface of the electrode pad connected to the connection conductor portion is lower than a height of a lower surface of the lower electrode.

Also, another ultrasonic probe according to the embodiment includes a semiconductor chip in which an ultrasonic transducer including a lower electrode, a cavity portion disposed so as to overlap with the lower electrode in a plan view, and an upper electrode disposed so as to overlap with the cavity portion in a plan view is formed and an electrode pad electrically connected to the lower electrode or the upper electrode is formed. The ultrasonic probe further includes a flexible substrate provided with a connection conductor portion electrically connected to the electrode pad, and a height of a connection surface of the electrode pad connected to the connection conductor portion is lower than a height of a lower surface of the lower electrode.

Also, an ultrasonic measurement apparatus according to the embodiment includes an ultrasonic probe including a semiconductor chip in which an ultrasonic transducer is formed and an electrode pad connected to an upper electrode or a lower electrode of the ultrasonic transducer is provided and a flexible substrate in which a connection conductor portion connected to the electrode pad is provided and the connection conductor portion is disposed in a portion overlapping with a part of the semiconductor chip in a plan view. The ultrasonic measurement apparatus further includes a control unit configured to control transmission and reception of ultrasonic waves of the ultrasonic probe, and a height of a connection surface of the electrode pad of the semiconductor chip connected to the connection conductor portion of the flexible substrate is lower than a height of a lower surface of the lower electrode of the semiconductor chip.

Effects of the Invention

The effects obtained by typical invention disclosed in this application will be briefly described as follows.

It is possible to facilitate the alignment at the time of flip-chip bonding between a semiconductor chip and a flexible substrate. Also, it is possible to improve measurement accuracy by an ultrasonic probe and an ultrasonic measurement apparatus.

BRIEF DESCRIPTIONS OF THE DRAWINGS

DETAILED DESCRIPTION OF PREFERRED EMBODIMENTS

Figure 1:
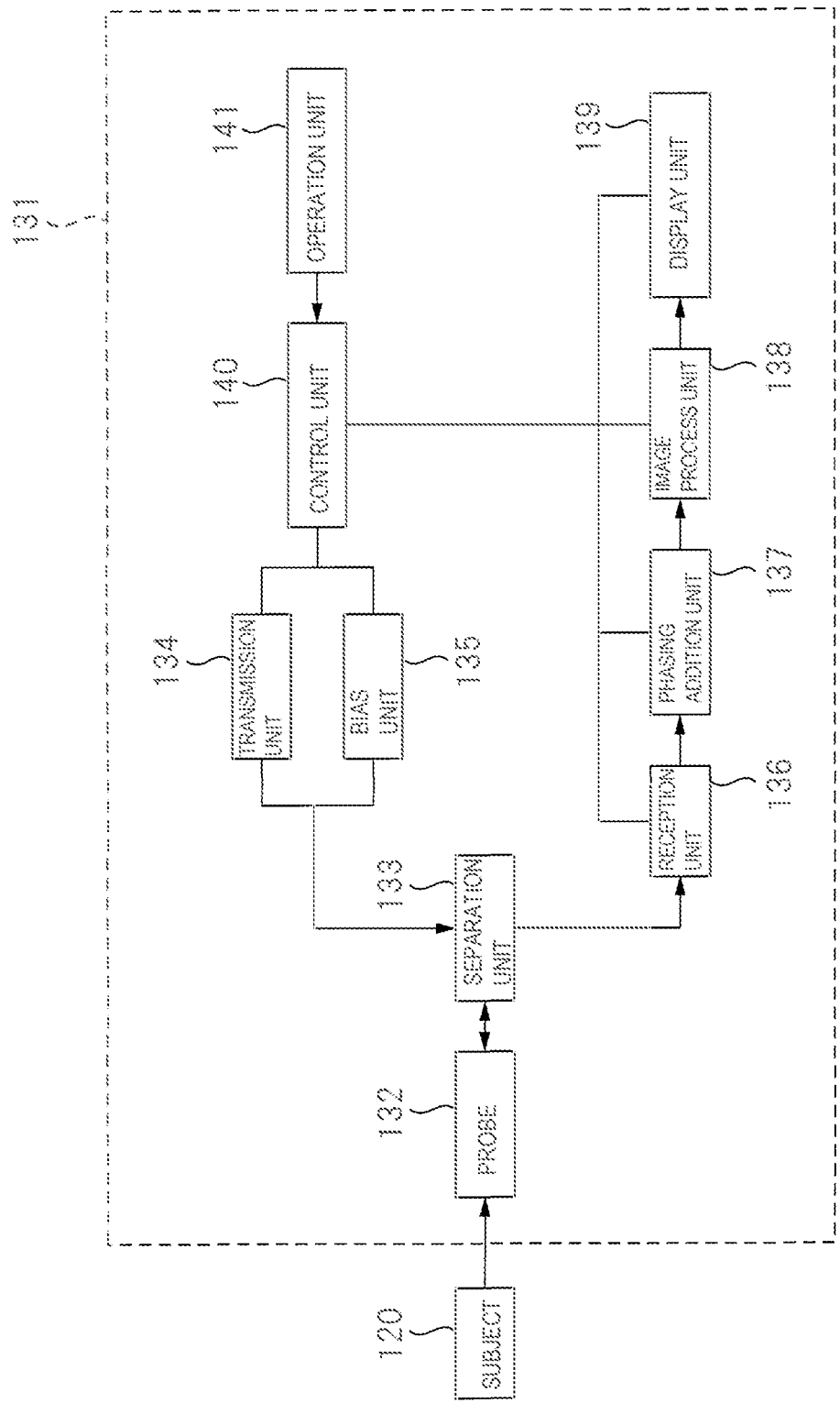
FIG. 1 is a schematic diagram showing an example of a configuration of an ultrasonic measurement apparatus according to an embodiment of the present invention.

FIG. 1 is a schematic diagram showing an example of a configuration of an ultrasonic measurement apparatus according to an embodiment of the present invention.

In the ultrasonic measurement apparatus according to the embodiment, an ultrasonic probe which is a probe is brought into contact with a surface of a living body to radiate ultrasonic waves, and reflected waves (ultrasonic waves) returned from organs, blood vessels, and the like are detected to image them.

A configuration of an ultrasonic measurement apparatus 131 provided with an ultrasonic probe 132 and functions of respective units will be described with reference to FIG. 1. The ultrasonic measurement apparatus 131 includes a transmission/reception separation unit 133, a transmission unit 134, a bias unit 135, a reception unit 136, a phasing addition unit 137, an image processing unit 138, a display unit 139, a control unit 140, and an operation unit 141 in addition to the ultrasonic probe 132.

Note that the ultrasonic probe 132 is a device that is brought into contact with a subject 120 to transmit and receive ultrasonic waves to and from the subject 120, and is formed by using an ultrasonic transducer. Namely, ultrasonic waves are transmitted from the ultrasonic probe 132 to the subject 120, and reflected echo signals from the subject 120 are received by the ultrasonic probe 132. Further, the ultrasonic probe 132 is electrically connected to the transmission/reception separation unit 133.

Also, the transmission unit 134 and the bias unit 135 are devices that supply drive signals to the ultrasonic probe 132, and the reception unit 136 is a device that receives reflected echo signals output from the ultrasonic probe 132. Further, the reception unit 136 performs a process such as analog-to-digital conversion to the received reflected echo signals.

Note that the transmission/reception separation unit 133 switches and separates transmission and reception so as to pass the drive signals from the transmission unit 134 to the ultrasonic probe 132 during transmission and to pass reception signals from the ultrasonic probe 132 to the reception unit 136 during reception. Also, the phasing addition unit 137 is a device that performs phasing addition of the received reflected echo signals, and the image processing unit 138 is a device that forms measurement images (for example, tomographic images and blood flow images) based on the reflected echo signals subjected to the phasing addition.

In addition, the display unit 139 is a display device that displays the measurement images subjected to the image processing. Also, the control unit 140 is a device that controls each of the above-described components, and mainly controls transmission and reception of ultrasonic waves of the ultrasonic probe 132. Further, the operation unit 141 is a device that gives an instruction to the control unit 140, and is, for example, an input device such as a trackball, a keyboard, and a mouse.

Here, in this embodiment, the case where the ultrasonic transducer is a capacitive micro-machined ultrasonic transducer (hereinafter, simply referred to also as a CMUT 102) will be described. The CMUT 102 is an ultrasonic transducer formed in a semiconductor chip 101 by a semiconductor process.

Figure 2:
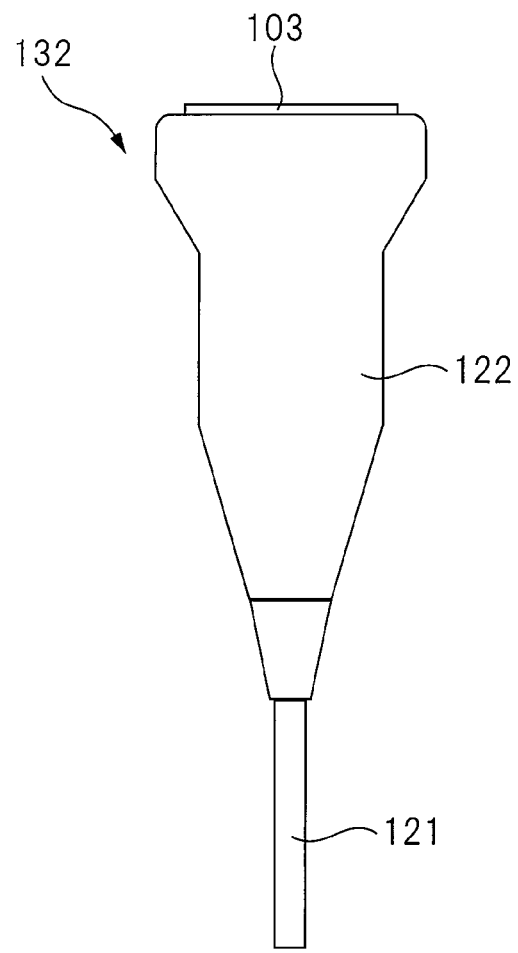
FIG. 2 is a partial side view showing an example of an external structure of an ultrasonic probe according to the embodiment of the present invention.
Figure 3:
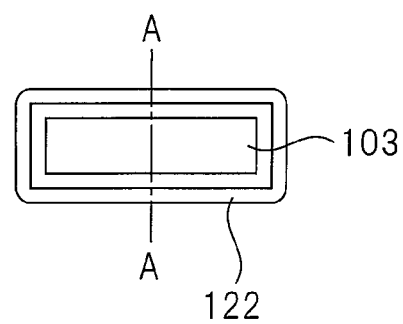
FIG. 3 is a plan view showing an example of the external structure of the ultrasonic probe shown in FIG. 2.

Next, the ultrasonic probe 132 which is a probe provided in the ultrasonic measurement apparatus 131 of this embodiment will be described. FIG. 2 is a partial side view showing an example of an external structure of the ultrasonic probe according to the embodiment of the present invention, FIG. 3 is a plan view showing an example of the external structure of the ultrasonic probe shown in FIG. 2, and FIG. 4 is a partially enlarged cross-sectional view showing the structure taken along the line A-A shown in FIG. 3.

Figure 9:
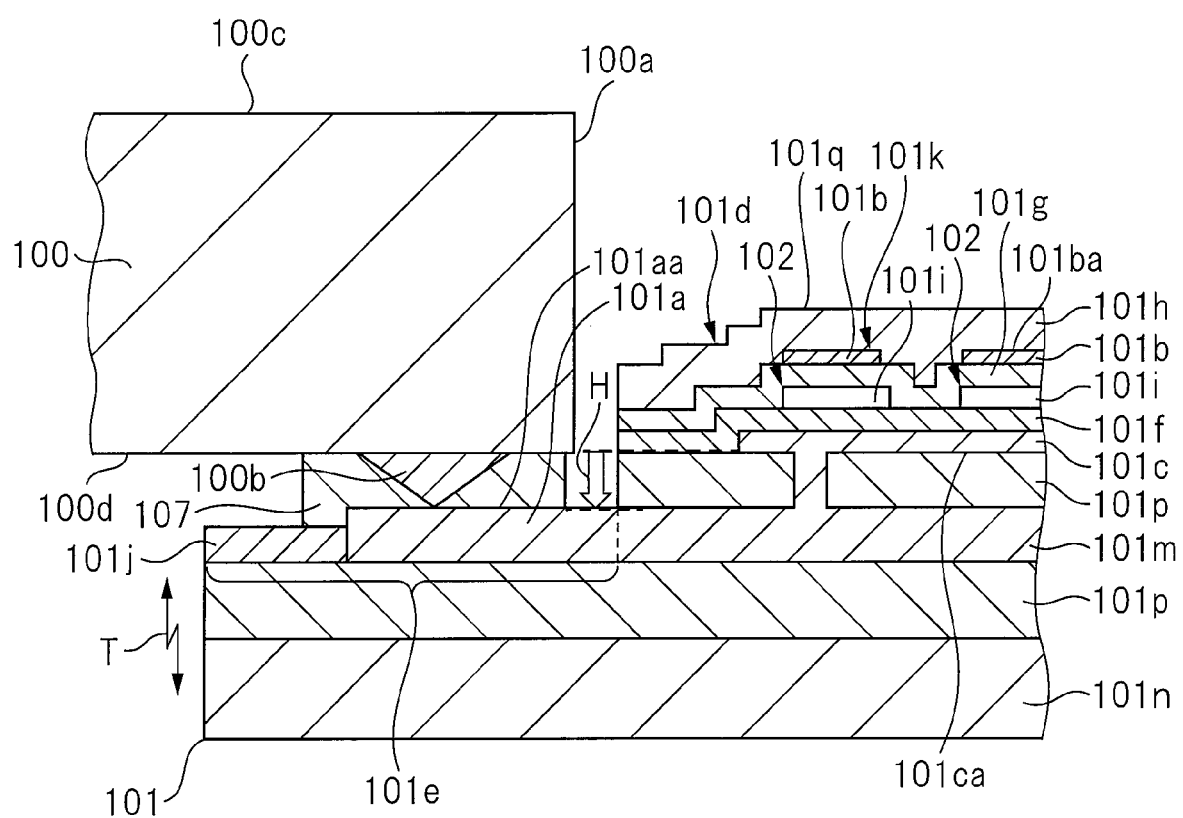
FIG. 9 is a partially enlarged cross-sectional view showing the structure taken along the line A-A shown in FIG. 8.

The ultrasonic probe 132 of this embodiment shown in FIG. 2 includes the semiconductor chip 101 in which the CMUT 102 described later with reference to FIG. 9 is formed and an electrode pad 101a electrically connected to an upper electrode 101b or a lower electrode 101c of the CMUT 102 is provided. The ultrasonic probe 132 further includes a flexible substrate 100 in which a connection conductor portion electrically connected to the electrode pad 101a is provided and the connection conductor portion is disposed in a portion overlapping with a part of the semiconductor chip 101 in a plan view. Note that the flexible substrate 100 is referred to also as a flexible printed board, a flexible printed wiring board, or the like.

Figure 4:
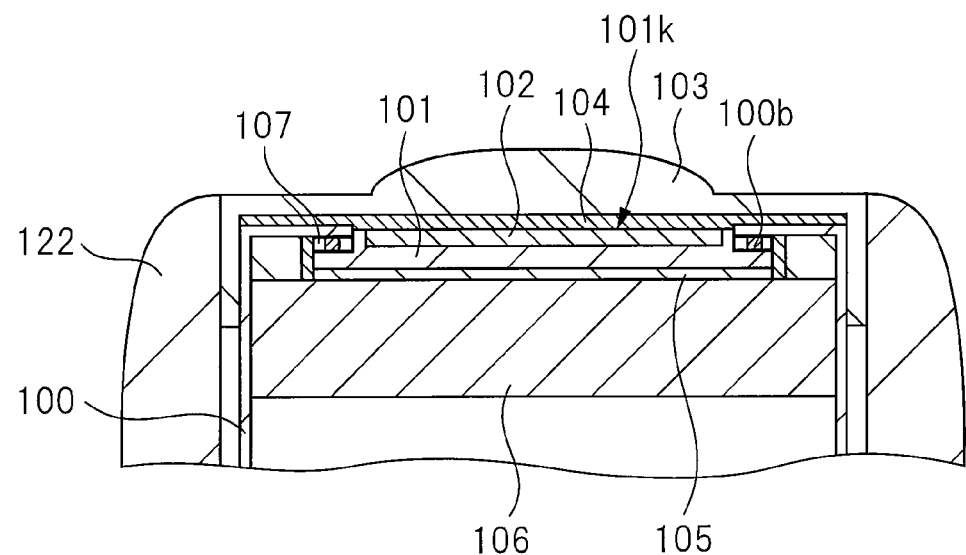
FIG. 4 is a partially enlarged cross-sectional view showing the structure taken along the line A-A shown in FIG. 3.

Further, as shown in FIG. 4, the ultrasonic probe 132 includes a backing material 106 for supporting the semiconductor chip 101 and an acoustic lens 103 disposed on the semiconductor chip 101.

Here, the CMUT 102, which is an ultrasonic transducer, is a MEMS (Micro Electro Mechanical Systems) capacitive ultrasonic transducer, and when a voltage is applied to the upper electrode 101b and the lower electrode 101c of the CMUT 102, an electrostatic attraction force is generated between the upper electrode 101b and the lower electrode 101c, and a membrane including the upper electrode 101b disposed above a cavity portion 101i vibrates to generate ultrasonic waves. On the other hand, when ultrasonic waves are externally applied to the membrane, the membrane is deformed, so that the electrostatic capacitance between the upper electrode 101b and the lower electrode 101c changes.

Also, the flexible substrate 100 is a thin-film substrate having flexibility, and is made of, for example, a material such as polyimide, polyamide imide, or polyethylene terephthalate, and has a thickness of, for example, about 0.1 mm.

Also, the backing material 106 is a member that supports the semiconductor chip 101 and is provided on the back side of the CMUT 102 (the side opposite to the ultrasonic transmission side). The backing material 106 is configured to absorb the ultrasonic waves transmitted to the back side of the CMUT 102, thereby shortening the pulse width of the ultrasonic waves and improving the distance resolution in an image.

Also, the acoustic lens 103 is disposed on the CMUT 102 formed in the semiconductor chip 101, and is configured to align the focal point of the ultrasonic sound.

Further, members such as the acoustic lens 103, the semiconductor chip 101 having the CMUT 102 formed therein, the flexible substrate 100, and the backing material 106 are housed in a case 122 made of resin. Also, a plurality of wirings led out from the flexible substrate 100 are housed in a cable 121 shown in FIG. 2. When the ultrasonic probe 132 is viewed from its tip end side, the tip end side of the case 122 is covered with the acoustic lens 103 as shown in FIG. 3 and FIG. 4.

Also, in the case 122 of the ultrasonic probe 132, the semiconductor chip 101 is fixed to the backing material 106 by an adhesive film 105 as shown in FIG. 4. Further, the acoustic lens 103 is fixed to the flexible substrate 100 and the semiconductor chip 101 by an adhesive 104. In addition, an insulating resin 107 is filled around a bump 100b, which is a connection portion between the flexible substrate 100 and the semiconductor chip 101 (the connection portion for flip-chip bonding).

Figure 12:
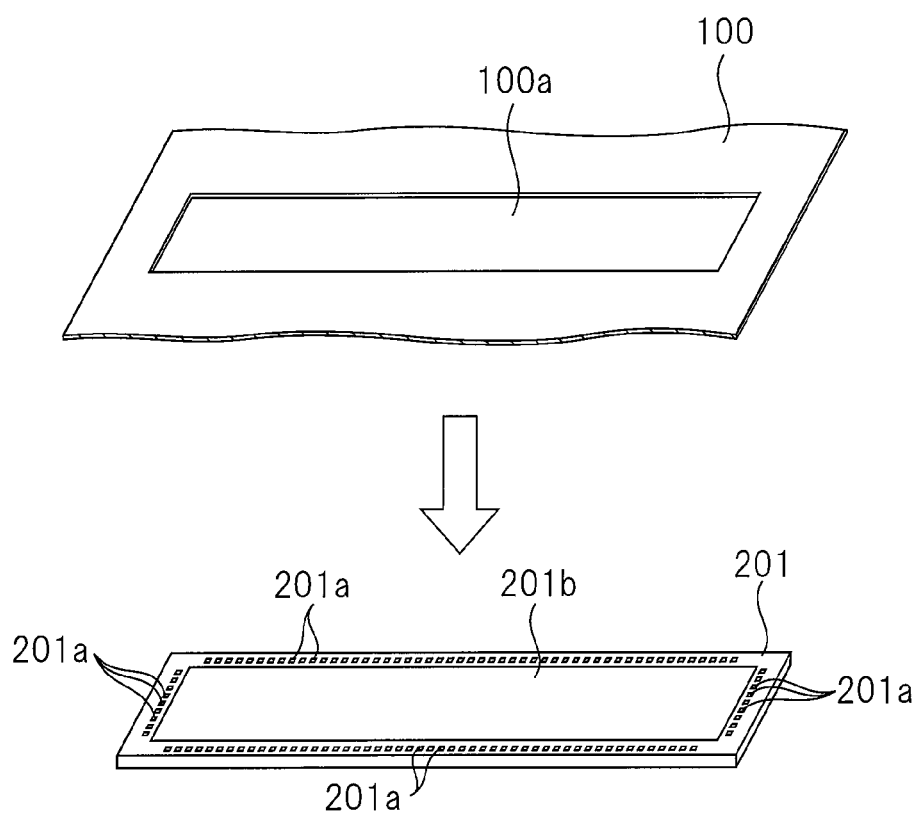
FIG. 12 is a perspective view showing in a partially broken manner a method of fitting a flexible substrate and a semiconductor chip in an ultrasonic probe according to a comparative example used for comparison and study by the inventors of the present invention.

Next, a comparative example studied by the inventors of the present invention will be described. FIG. 12 is a perspective view showing in a partially broken manner a method of fitting a flexible substrate and a semiconductor chip in an ultrasonic probe according to a comparative example used for comparison and study by the inventors of the present invention, FIG. 13 is a perspective view showing in a partially broken manner the structure after the flexible substrate and the semiconductor chip shown in FIG. 12 are fit, and FIG. 14 is a partially enlarged cross-sectional view showing the structure taken along the line A-A shown in FIG. 13.

Figure 13:
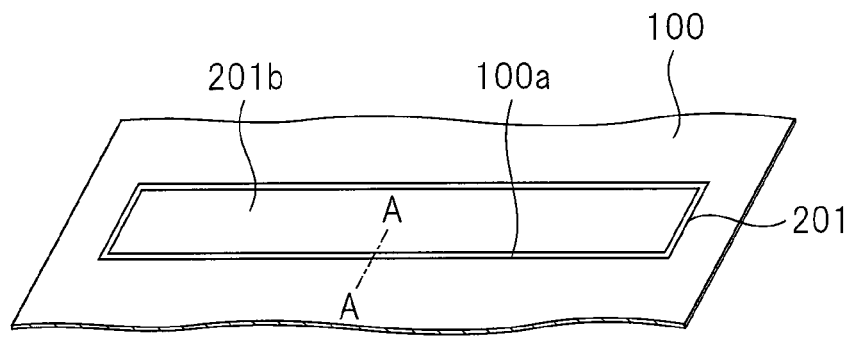
FIG. 13 is a perspective view showing in a partially broken manner the structure after the flexible substrate and the semiconductor chip shown in FIG. 12 are fit.
Figure 14:
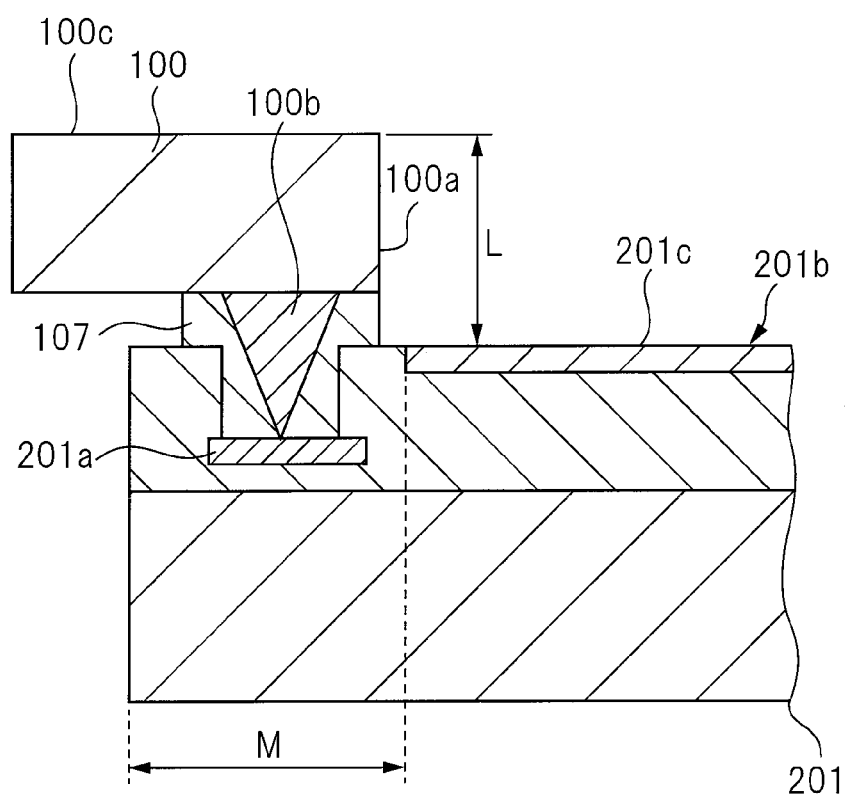
FIG. 14 is a partially enlarged cross-sectional view showing the structure taken along the line A-A shown in FIG. 13.

As shown in FIG. 12 to FIG. 14, when the flexible substrate 100 is bonded to the semiconductor chip 201, the flexible substrate 100 and the semiconductor chip 201 are aligned and bonded so that a CMUT cell region 201b of the semiconductor chip 201 is disposed in an opening 100a of the flexible substrate 100 as shown in FIG. 13 and FIG. 14.

At this time, in the flip-chip bonding, it is necessary to align each of the plurality of bumps (connection conductor portions) 100b of the flexible substrate 100 with each of the plurality of electrode pads 201a of the semiconductor chip 201. In the semiconductor chip 201, for example, about two hundred electrode pads 201a are formed in total on the four sides around the CMUT cell region 201b as shown in FIG. 12.

Therefore, one problem is that it is difficult to align the plurality of electrode pads 201a of the semiconductor chip 201 with the plurality of bumps 100b of the flexible substrate 100.

Further, in this case, it is possible to reduce the difficulty of the alignment by increasing the pad diameter of the electrode pads 201a of the semiconductor chip 201. However, if the pad diameter of the electrode pads 201a is increased, the chip size increases. Specifically, the distance of a portion M (flip-chip bonding portion) of the semiconductor chip 201 shown in FIG. 14 becomes long, and it is not possible to reduce the size of the semiconductor chip 201.

As a result, the size of the ultrasonic probe increases. Namely, another problem is that it is not possible to reduce the size of the ultrasonic probe.

Further, in the structure of the ultrasonic probe, the lens (the portion of the acoustic lens 103 on a CMUT cell region 101k shown in FIG. 4) disposed on the CMUT cell region 201b preferably has a small thickness. This is because since the acoustic lens 103 absorbs sound, the sound transmitted from the semiconductor chip 201 is attenuated while passing through the acoustic lens 103. Therefore, as long as the acoustic lens 103 disposed on the CMUT cell region 201b can focus the ultrasonic sound to a desired focal point, it is preferable that the acoustic lens 103 is as thin as possible in order to reduce attenuation.

Namely, in the structure shown in FIG. 14, it is preferable that the height difference (the distance of a portion L in FIG. 14) between an upper surface 100c of the flexible substrate 100 and a front surface 201c of the semiconductor chip 201 is reduced as much as possible, whereby the thickness of the acoustic lens 103 disposed on the CMUT cell region 201b is reduced as much as possible.

Therefore, the ultrasonic probe 132 of this embodiment is configured so that it is possible to automatically and easily align the bumps (connection conductor portions) 100b of the flexible substrate 100 and the electrode pads 101a of the semiconductor chip 101, and it is also possible to reduce the size of the ultrasonic probe 132. Further, it is possible to install the acoustic lens 103 having a small thickness.

Figure 5:
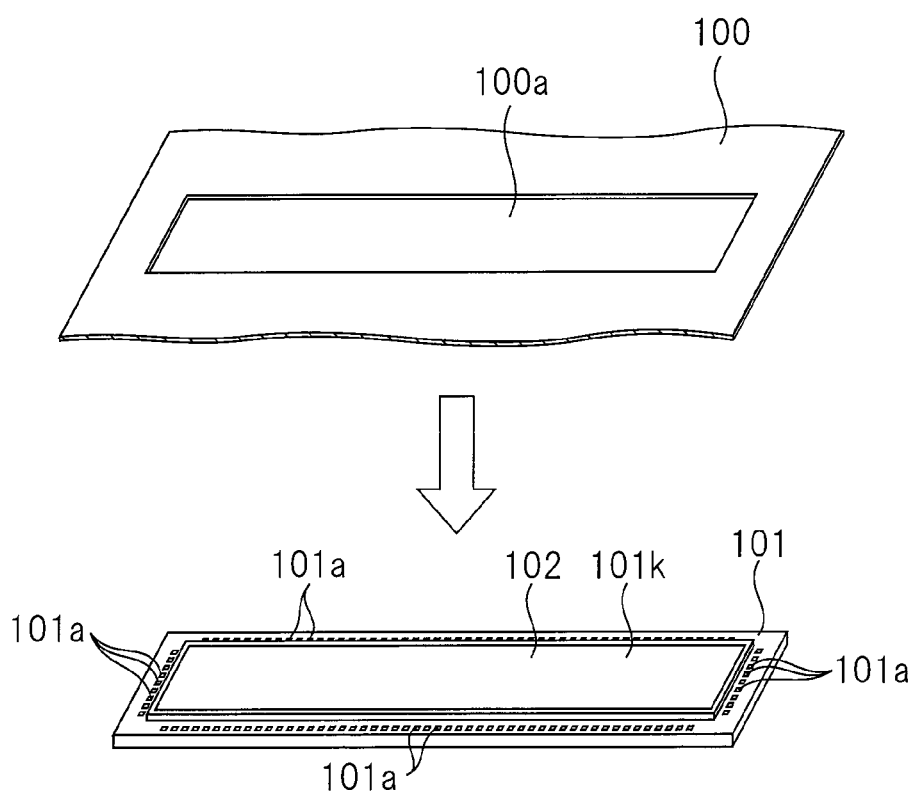
FIG. 5 is a perspective view showing in a partially broken manner an example of a method of fitting the flexible substrate and the semiconductor chip in the ultrasonic probe shown in FIG. 4.
Figure 6:
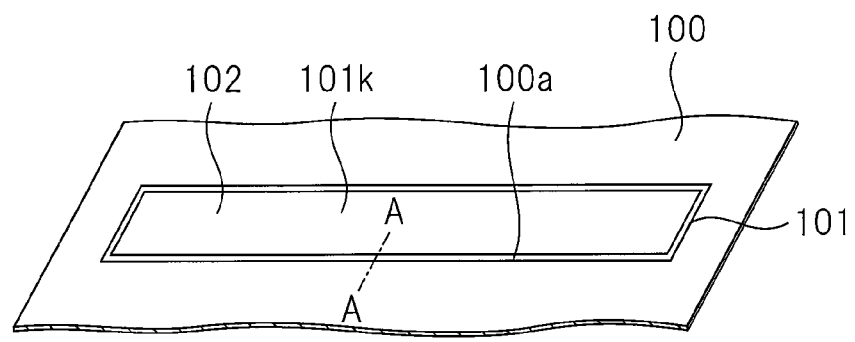
FIG. 6 is a perspective view showing in a partially broken manner an example of the structure after the flexible substrate and the semiconductor chip shown in FIG. 5 are fit.

Features of the ultrasonic probe 132 of this embodiment will be described with reference to FIG. 4 to FIG. 7. FIG. 5 is a perspective view showing in a partially broken manner an example of a method of fitting the flexible substrate and the semiconductor chip in the ultrasonic probe shown in FIG. 4, FIG. 6 is a perspective view showing in a partially broken manner an example of the structure after the flexible substrate and the semiconductor chip shown in FIG. 5 are fit, and FIG. 7 is a partially enlarged cross-sectional view showing the structure taken along the line A-A shown in FIG. 6.

Figure 7:
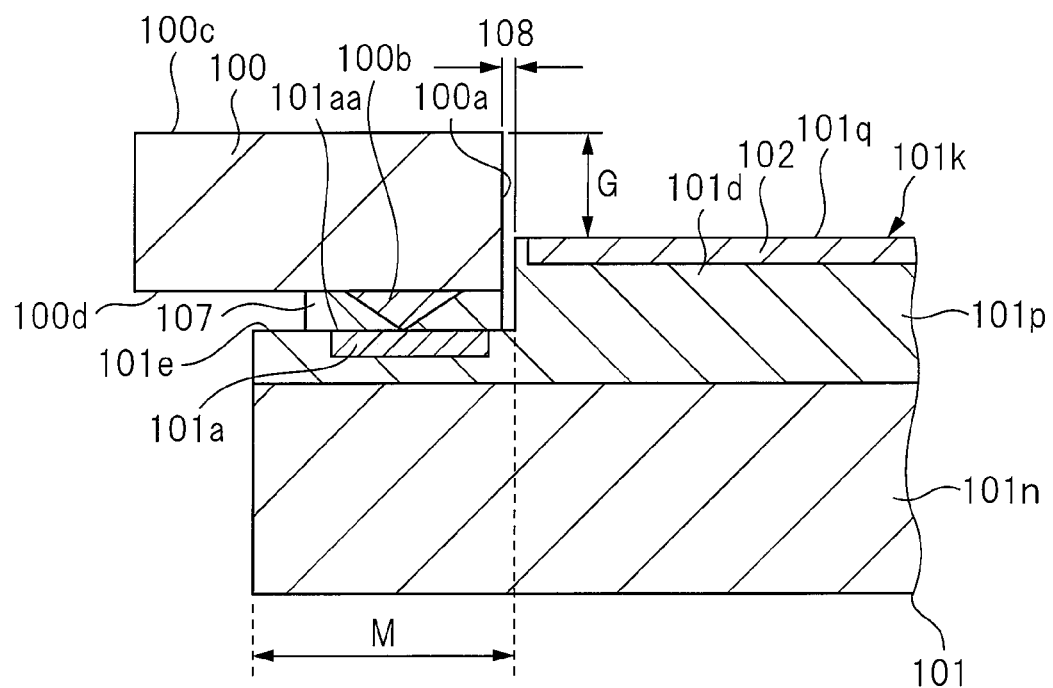
FIG. 7 is a partially enlarged cross-sectional view showing the structure taken along the line A-A shown in FIG. 6.

As shown in FIG. 7, in the semiconductor chip 101 of this embodiment, the CMUT cell region 101k is higher than a stepped portion 101e around the CMUT cell region 101k and forms a convex portion 101d. In other words, in the semiconductor chip 101, the height of the region around the CMUT cell region 101k is lower than that of the CMUT cell region 101k on the side of a front surface (main surface) 101q of the semiconductor chip 101. Namely, the semiconductor chip 101 has in its periphery the stepped portion 101e whose height is lower than that of the CMUT cell region 101k.

Then, the flexible substrate 100 extends (is disposed) along the stepped portion (peripheral portion) 101e whose height is lower than that of the CMUT cell region 101k of the semiconductor chip 101. Namely, the flexible substrate 100 and the semiconductor chip 101 are flip-chip bonded in the stepped portion 101e whose height is lower than that of the CMUT cell region 101k. At this time, the flexible substrate 100 is disposed so as to overlap with a part of the semiconductor chip 101 (the stepped portion 101e), and the bumps 100b serving as the connection conductor portions are arranged in this part of the flexible substrate 100 overlapping with the stepped portion 101e of the semiconductor chip 101.

Consequently, in the ultrasonic probe 132 of this embodiment, as shown in FIG. 9 described later, the height of a connection surface 101aa of the electrode pad 101a of the semiconductor chip 101 connected to the bump 100b is lower than that of a lower surface 101ca of the lower electrode 101c.

Note that, in the ultrasonic probe 132 of this embodiment, as shown in FIG. 5 and FIG. 6, when the flexible substrate 100 is connected to the semiconductor chip 101 (flip-chip bonding), they are connected so that the convex portion 101d in which the CMUT cell region 101k of the semiconductor chip 101 is formed is disposed in the rectangular opening 100a of the flexible substrate 100. Namely, the opening 100a of the flexible substrate 100 is fit with the convex portion 101d of the semiconductor chip 101 shown in FIG. 7. At this time, the opening 100a of the flexible substrate 100 is formed to have the size in which a gap 108 shown in FIG. 7 between the opening 100a and the convex portion 101d of the semiconductor chip 101 is about 40 to 50 µm in a plan view.

Thus, the flexible substrate 100 and the semiconductor chip 101 can be automatically and easily aligned simply by fitting the opening 100a of the flexible substrate 100 with the convex portion 101d of the semiconductor chip 101.

Then, the flip-chip bonding between the flexible substrate 100 and the semiconductor chip 101 is performed based on this alignment. Namely, the semiconductor chip 101 and the flexible substrate 100 are electrically connected via the bumps (connection conductor portions) 100b. At this time, as shown in FIG. 7, by applying an insulating resin 107 on the electrode pads 101a of the semiconductor chip 101 in advance, the insulating resin 107 is disposed around the bumps 100b after the flip-chip bonding. Namely, the insulating resin 107 is disposed around each bump 100b in the region between the flexible substrate 100 and the semiconductor chip 101, and it is possible to protect each flip-chip bonding portion. Note that, as the insulating resin 107, a film-shaped insulating resin 107 may be disposed on the electrode pads 101a of the semiconductor chip 101 in advance. Further, an anisotropic conductive film such as ACF may be used for the electrical connection instead of the bumps 100b. In this case, since the ACF also serves as the insulating resin 107, the step of applying the insulating resin 107 can be omitted.

As described above, in the ultrasonic probe 132 of this embodiment, even when about two hundred electrode pads 101a are formed along the four sides on the main surface (front surface 101q) of the semiconductor chip 101, it is only necessary to fit the opening 100a of the flexible substrate 100 with the convex portion 101d of the semiconductor chip 101 for the flip-chip bonding of the semiconductor chip 101. In this manner, the flexible substrate 100 and the semiconductor chip 101 can be aligned automatically and easily.

Figure 8:
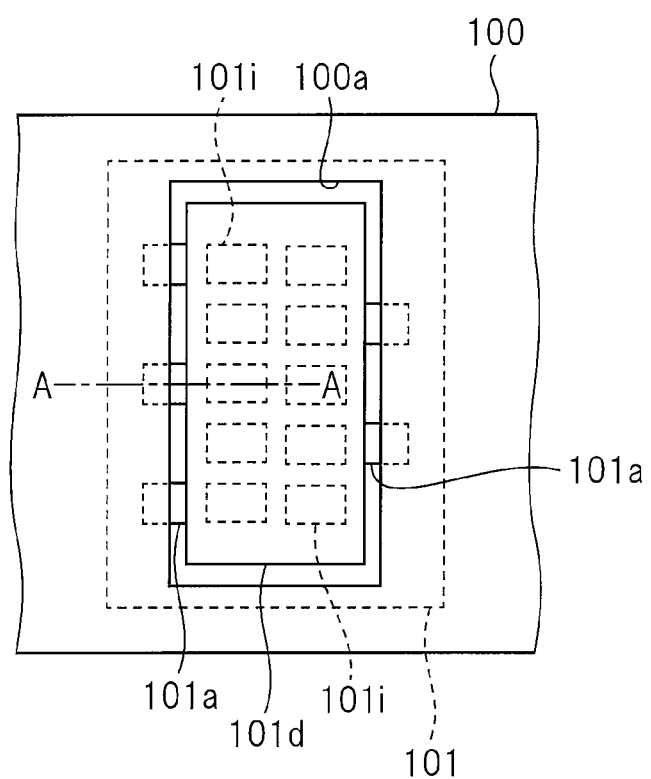
FIG. 8 is a partial plan view showing an example of the structure after the flexible substrate and the semiconductor chip are fit according to the embodiment of the present invention.

Next, a detailed connection structure between the semiconductor chip 101 and the flexible substrate 100 in the ultrasonic probe 132 of this embodiment will be described with reference to FIG. 8 and FIG. 9. FIG. 8 is a partial plan view showing an example of the structure after the flexible substrate and the semiconductor chip are fit according to the embodiment of the present invention, and FIG. 9 is a partially enlarged cross-sectional view showing the structure taken along the line A-A shown in FIG. 8.

As shown in FIG. 8, in the connection structure between the semiconductor chip 101 and the flexible substrate 100, the direction in which the flexible substrate 100 extends is a direction along each of any two or more sides of the four sides of the main surface of the semiconductor chip 101. In this embodiment, the flexible substrate 100 extends along each of the four sides of the main surface of the semiconductor chip 101. However, the flexible substrate 100 only needs to extend along at least two sides of the four sides of the main surface of the semiconductor chip 101.

Further, the flexible substrate 100 has the opening 100a opened from the front surface to the back surface thereof, and the convex portion 101d in which the CMUT 102 of the semiconductor chip 101 is formed is disposed in the opening 100a of the flexible substrate 100 as shown in FIG. 9. In other words, the four sides of the CMUT cell region 101k formed in the convex portion 101d of the semiconductor chip 101 are surrounded by the flexible substrate 100 in a plan view. Then, as shown in FIG. 4, the acoustic lens 103 is disposed on the CMUT cell region 101k of the convex portion 101d.

Note that, as shown in FIG. 8 and FIG. 9, a lower electrode 101c, a first insulating film 101f that covers the lower electrode 101c, a cavity portion 101i disposed to overlap with the lower electrode 101c in a plan view, a second insulating film 101g that covers the cavity portion 101i, the upper electrode 101b disposed to overlap with the cavity portion 101i in a plan view, and a third insulating film 101h that covers the upper electrode 101b are formed in the convex portion 101d of the semiconductor chip 101. Then, a plurality of the CMUTs 102 each having the lower electrode 101c, the upper electrode 101b, and the cavity portion 101i are formed in the convex portion 101d, thereby forming the CMUT cell region 101k.

In addition, the plurality of electrode pads 101a that are electrically connected to the lower electrode 101c or the upper electrode 101b are formed in the stepped portion 101e, which is a region outside the convex portion 101d of the semiconductor chip 101. FIG. 9 shows the structure in which the lower electrode 101c and the electrode pad 101a are electrically connected via a wiring 101m. Note that the electrode pads 101a only need to be disposed in the stepped portion (peripheral portion) 101e along at least one side of the front surface (main surface) 101q of the semiconductor chip 101, and the electrode pads 101a are provided along two opposing long sides of the four sides of the front surface (main surface) 101q of the semiconductor chip 101 in the structure shown in FIG. 8, and are provided in the stepped portion 101e shown in FIG. 9.

Also, the height of the connection surface 101aa of the electrode pad 101a connected to the bump 100b is lower than the height of the lower surface 101ca of the lower electrode 101c (portion H shown in FIG. 9). In other words, in the semiconductor chip 101, the chip thickness of the stepped portion (pad region) 101e on the outer periphery of the chip, which is the peripheral portion of the chip on which the plurality of electrode pads 101a are formed, is smaller than that of the convex portion 101d in which the CMUT cell region 101k is formed.

In addition, a lower surface 100d of the flexible substrate 100 opposite to the upper surface 100c is located between an upper surface 101ba of the upper electrode 101b of the semiconductor chip 101 and the connection surface (upper surface) 101aa of the electrode pad 101a in the thickness direction of the semiconductor chip 101 (direction T shown in FIG. 9).

Further, an outer peripheral insulating film 101j is formed at a position outside the electrode pad 101a of the semiconductor chip 101, and a front surface of the outer peripheral insulating film 101j has the same height as the connection surface 101aa of the electrode pad 101a or has the height lower than the connection surface 101aa of the electrode pad 101a. In the structure shown in FIG. 9, the case where the front surface of the outer peripheral insulating film 101j has the height lower than the connection surface 101aa of the electrode pad 101a is illustrated.

Consequently, it is possible to reduce the occurrence of a fault that causes a bump connection failure at the time of the flip-chip bonding. For example, it is possible to suppress the occurrence of connection failure due to that the flexible substrate 100 contacts the edge portion of the semiconductor chip 101 before the bump 100b is connected to the electrode pad 101a.

Note that the height of the convex portion 101d (part above the wiring 101m) in the semiconductor chip 101 is, for example, about several μm. Also, the height on the side of the flexible substrate 100 above the electrode pad 101a, that is, the height obtained by adding the thickness of the flexible substrate 100 to the height of the bump 100b is, for example, a little more than 10 μm to 50 μm. Therefore, the difference between the height of the upper surface 100c of the flexible substrate 100 and the height of the front surface 101q of the convex portion 101d of the semiconductor chip 101 (distance G in FIG. 7) can be made much smaller than the thickness of the flexible substrate 100.

Further, in the structure shown in FIG. 8, the plurality of electrode pads 101a are led out and arranged by the wirings 101m (see FIG. 9) on each of the two opposing sides (long sides) of the main surface of the semiconductor chip 101. At this time, if the number of lead wirings 101m is large, the number of channels is increased, and the focus of ultrasonic waves can be made finer.

Here, the wiring 101m and the electrode pad 101a are formed on a silicon substrate 101n via an insulating film 101p.

Further, by leading out and arranging the electrode pads 101a on the two opposing sides of the main surface of the semiconductor chip 101 (on both sides of the main surface of the semiconductor chip 101) as is the structure shown in FIG. 8, the wirings 101m are disposed on both sides and the voltage drop is uniformized, so that the sound quality balance can be improved.

According to the ultrasonic probe 132 of this embodiment, in the semiconductor chip 101, the chip thickness of the stepped portion (pad region) 101e on the outer peripheral portion of the chip is made smaller than the chip thickness of the portion including the convex portion 101d in which the CMUT cell region 101k is formed, so that the flexible substrate 100 can be disposed to extend on the stepped portion 101e.

In this manner, when the flexible substrate 100 and the semiconductor chip 101 are flip-chip bonded via the bumps 100b, the flexible substrate 100 and the semiconductor chip 101 can be automatically and easily aligned simply by fitting the opening 100a of the flexible substrate 100 with the convex portion 101d of the semiconductor chip 101.

Further, since the semiconductor chip 101 and the flexible substrate 100 can be easily aligned, the size of each of the plurality of electrode pads 101a can be reduced, and the stepped portion 101e (protruding portion) of the peripheral portion of the semiconductor chip 101 can be narrowed. As a result, the size of the ultrasonic probe 132 can be reduced.

In addition, since it is possible to reduce the difference between the height of the upper surface 100c of the flexible substrate 100 and the height of the front surface 101q of the convex portion 101d of the semiconductor chip 101 (the distance G in FIG. 7), a part of the acoustic lens 103 disposed on the convex portion 101d can be made thinner.

In this manner, the acoustic pressure of the ultrasonic waves can be improved, and the frequency of the ultrasonic waves can be increased. Namely, since the thickness of the portion of the acoustic lens 103 through which the ultrasonic waves pass can be reduced, the acoustic pressure can be improved, and the magnitude of the reflected echo signal to be acquired can be increased. As a result, a small lesion of the subject 120 can be found in the ultrasonic probe 132 and the ultrasonic measurement apparatus 131.

Further, when the thickness of the portion of the acoustic lens 103 through which the ultrasonic waves pass is reduced, the frequency of the ultrasonic waves can be increased, and the resolution of the reflected echo signals to be acquired can be improved. In this manner, the measurement accuracy (inspection accuracy) in the ultrasonic probe 132 and the ultrasonic measurement apparatus 131 can be improved.

Figure 10:
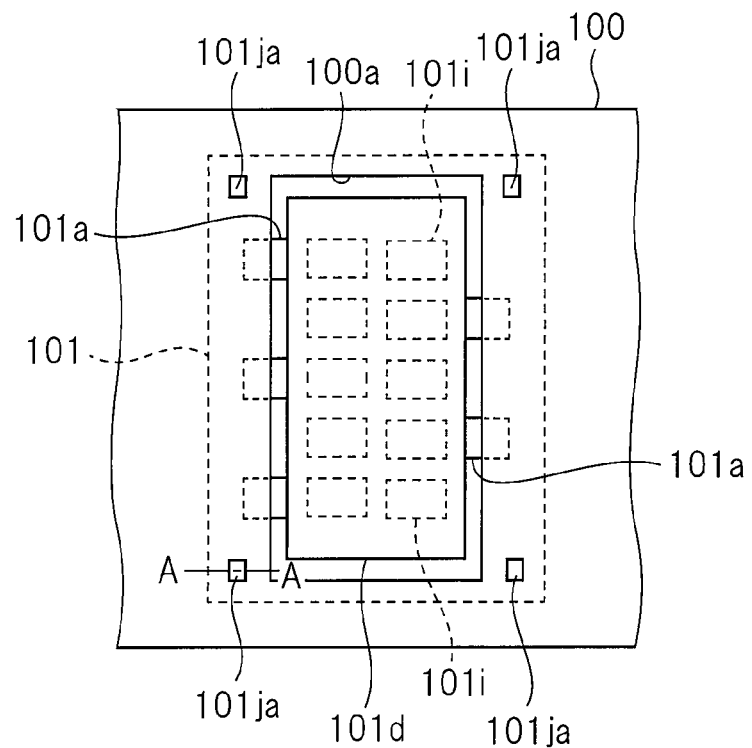
FIG. 10 is a partial plan view showing the structure after a flexible substrate and a semiconductor chip are fit according to a modification of the embodiment of the present invention.

Next, a modification of this embodiment will be described. FIG. 10 is a partial plan view showing the structure after a flexible substrate and a semiconductor chip are fit according to a modification of the embodiment of the present invention, and FIG. is a partially enlarged cross-sectional view showing the structure taken along the line A-A shown in FIG. 10.

Figure 11:
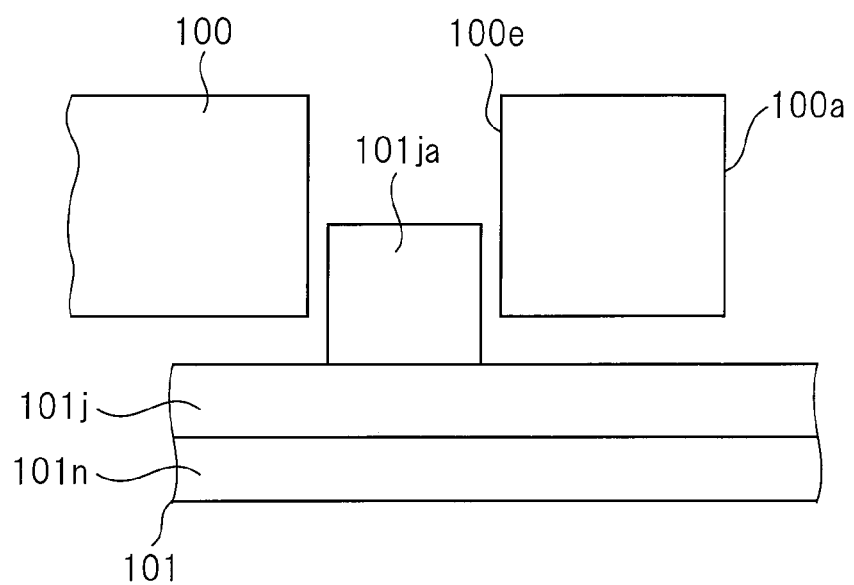
FIG. 11 is a partially enlarged cross-sectional view showing the structure taken along the line A-A shown in FIG. 10.

In the modification shown in FIG. 10 and FIG. 11, a plurality of through holes 100e are formed around the opening 100a of the flexible substrate 100, and a plurality of projecting portions 101ja are formed on the outer peripheral insulating film 101j of the semiconductor chip 101 (though the number of projecting portions 101ja is four in this modification, any number of projecting portions 101ja may be provided as long as the number is two or more). Further, each of the plurality of projecting portions 101ja of the semiconductor chip 101 is fit into each of the plurality of through holes 100e of the flexible substrate 100.

Consequently, when the semiconductor chip 101 is flip-chip bonded to the flexible substrate 100, they can be automatically and easily aligned by the projecting portions 101ja of the semiconductor chip 101 and the through holes 100e of the flexible substrate 100.

In the case of the structure shown in FIG. 10 and FIG. 11, since regions for forming the projecting portions 101ja are necessary in the semiconductor chip 101, the degree of the size reduction effect of the ultrasonic probe 132 is decreased as compared with the structure of the embodiment shown in FIG. 5 to FIG. 9. However, when compared with the structure of the comparative example shown in FIG. 12 to FIG. 14, since the size of each electrode pad 101a can be reduced, it is possible to reduce the size of the ultrasonic probe 132.

Note that the through hole 100e of the flexible substrate 100 into which the projecting portion 101ja of the semiconductor chip 101 shown in FIG. 11 is fit is not limited to the through hole 100e and may be a recess portion or the like as long as the projecting portion 101ja can be fit.

In the foregoing, the present invention is not limited to the embodiment described above and includes various modifications. For example, the above embodiment has described the present invention in detail in order to make the present invention easily understood, and the present invention is not necessarily limited to those having all the described configurations.

Also, a part of the configuration of one embodiment may be replaced with the configuration of another embodiment, and the configuration of one embodiment may be added to the configuration of another embodiment. Further, another configuration may be added to a part of the configuration of each embodiment, and a part of the configuration of each embodiment may be eliminated or replaced with another configuration. Note that each member and relative size thereof described in the drawings are simplified and idealized for easy understanding of the present invention, and have a more complicated shape in actual implementation.

For example, in the above embodiment, the case where the plurality of electrode pads 101a are formed along each of the four sides of the main surface of the semiconductor chip 101 shown in FIG. 5 has been described. Alternatively, the case where the plurality of electrode pads 101a are formed along each of the two opposing sides of the main surface of the semiconductor chip 101 as shown in FIG. 8 has been described. However, the plurality of electrode pads 101a may be formed along each of any three sides of the main surface of the semiconductor chip 101.

REFERENCE SIGNS LIST

100: flexible substrate
100a: opening
100b: bump (connection conductor portion)
100c: upper surface
100d: lower surface
100e: through hole
101: semiconductor chip
101a: electrode pad
101aa: connection surface (upper surface)
101b: upper electrode
101ba: upper surface
101c: lower electrode
101ca: lower surface
101d: convex portion
101e: stepped portion
101f: first insulating film
101g: second insulating film
101h: third insulating film
101i: cavity portion
101j: outer peripheral insulating film
101ja: projecting portion
101k: CMUT cell region
101m: wiring
101n: silicon substrate
101p: insulating film
101q: front surface
102: CMUT (capacitive micro-machined ultrasonic transducer)
103: acoustic lens
104: adhesive
105: adhesive film
106: backing material
107: insulating resin
108: gap
120: subject
121: cable
122: case
131: ultrasonic measurement apparatus
132: ultrasonic probe
133: transmission/reception separation unit
134: transmission unit
135: bias unit
136: reception unit
137: phasing addition unit
138: image processing unit
139: display unit
140: control unit
141: operation unit
201: semiconductor chip
201a: electrode pad
201b: CMUT cell region
201c: front surface

The invention claimed is:

1. An ultrasonic probe comprising:
a semiconductor chip in which an ultrasonic transducer is formed and an electrode pad electrically connected to an upper electrode or a lower electrode of the ultrasonic transducer is provided; and
a flexible substrate in which a connection conductor portion electrically connected to the electrode pad is provided and the connection conductor portion is disposed in a portion overlapping with a part of the semiconductor chip in a plan view,
wherein the electrode pad comprises a stepped portion disposed below the flexible substrate and a convex portion in which the ultrasonic transducer is formed,
wherein a height of a connection surface of the stepped portion of the electrode pad connected to the connection conductor portion is lower than a height of a lower surface of the lower electrode at the convex portion of the electrode pad, and
wherein a lower surface of the flexible substrate at the stepped portion of the electrode pad is located at a height between an upper surface of the upper electrode at the convex portion of the electrode pad in which the ultrasonic transducer is formed and an upper surface of the electrode pad at the stepped portion in the semiconductor chip, in a thickness direction of the semiconductor chip.

2. The ultrasonic probe according to claim 1,
wherein an upper surface of the stepped portion of the electrode pad is disposed at a position lower than an upper surface of the upper electrode at the convex portion of the electrode pad, and
wherein the flexible substrate is disposed above the stepped portion.

3. The ultrasonic probe according to claim 2,
wherein the flexible substrate extends in a plurality of directions along two or more sides of a main surface of the semiconductor chip.

4. The ultrasonic probe according to claim 1,
wherein the flexible substrate has an opening, and
wherein the convex portion in which the ultrasonic transducer of the semiconductor chip is formed is disposed in the opening.

5. The ultrasonic probe according to claim 4,
wherein an acoustic lens is disposed on the convex portion.

6. An ultrasonic probe comprising:

a semiconductor chip in which an ultrasonic transducer including a lower electrode, a first insulating film covering the lower electrode, a cavity portion disposed so as to overlap with the lower electrode in a plan view, a second insulating film covering the cavity portion, and an upper electrode disposed so as to overlap with the cavity portion in a plan view is formed and an electrode pad electrically connected to the lower electrode or the upper electrode is formed; and a flexible substrate provided with a connection conductor portion electrically connected to the electrode pad, wherein the electrode pad comprises a stepped portion disposed below the flexible substrate and a convex portion in which the ultrasonic transducer is formed, wherein a height of a connection surface of the stepped portion of the electrode pad connected to the connection conductor portion is lower than a height of a lower surface of the lower electrode at the convex portion of the electrode pad, wherein an outer peripheral insulating film is formed outside the electrode pad of the semiconductor chip, and wherein an upper surface of the outer peripheral insulating film has a same height as an upper surface of the electrode pad or has a height lower than the upper surface of the electrode pad.

7. The ultrasonic probe according to claim 6, wherein the electrode pad is provided in a peripheral portion along at least one side of an upper surface of the semiconductor chip.

8. The ultrasonic probe according to claim 6, wherein a plurality of through holes are formed in the flexible substrate, wherein a plurality of projecting portions are formed on the outer peripheral insulating film, and wherein each of the plurality of projecting portions are is fit into each of the plurality of through holes.

9. An ultrasonic measurement apparatus comprising:

an ultrasonic probe including a semiconductor chip in which an ultrasonic transducer is formed and an electrode pad electrically connected to an upper electrode or a lower electrode of the ultrasonic transducer is provided and a flexible substrate in which a connection conductor portion electrically connected to the electrode pad is provided and the connection conductor portion is disposed in a portion overlapping with a part of the semiconductor chip in a plan view; and a control unit configured to control transmission and reception of ultrasonic waves of the ultrasonic probe, wherein the electrode pad of the semiconductor chip comprises a stepped portion disposed below the flexible substrate and a convex portion in which the ultrasonic transducer is formed, wherein a height of a connection surface of the stepped portion of the electrode pad of the semiconductor chip connected to the connection conductor portion of the flexible substrate is lower than a height of a lower surface of the lower electrode of the semiconductor chip at the convex portion of the electrode pad, and wherein a lower surface of the flexible substrate at the stepped portion of the electrode pad is located at a height between an upper surface of the upper electrode at the convex portion of the electrode pad in which the ultrasonic transducer is formed and an upper surface of the electrode pad at the stepped portion in the semiconductor chip, in a thickness direction of the semiconductor chip.

10. The ultrasonic measurement apparatus according to claim 9, wherein an upper surface of the stepped portion of the electrode pad is disposed at a position lower than an upper surface of the upper electrode at the convex portion of the electrode pad, and wherein the flexible substrate is disposed above the stepped portion.

11. The ultrasonic measurement apparatus according to claim 10, wherein the flexible substrate extends in a plurality of directions along two or more sides of a main surface of the semiconductor chip.

12. The ultrasonic measurement apparatus according to claim 9, wherein the flexible substrate has an opening, and wherein the convex portion in which the ultrasonic transducer of the semiconductor chip is formed is disposed in the opening.

* * * * *